US011229672B2

(12) United States Patent
Lee et al.

(10) Patent No.: US 11,229,672 B2
(45) Date of Patent: Jan. 25, 2022

(54) PROBIOTICS COMPOSITION CONTAINING HERICIUM ERINACEUS

(71) Applicants: Dae Hee Lee, Cheongju-si (KR); CNG BIO CO., LTD., Cheongju-si (KR)

(72) Inventors: Dae Hee Lee, Cheongju-si (KR); Jae Kang Lee, Cheongju-si (KR)

(73) Assignees: Dae Hee Lee, Cheongju-si (KR); CNG BIO CO., LTD., Cheongju-si (KR)

( * ) Notice: Subject to any disclaimer, the term of this patent is extended or adjusted under 35 U.S.C. 154(b) by 142 days.

(21) Appl. No.: 16/337,263

(22) PCT Filed: Feb. 16, 2017

(86) PCT No.: PCT/KR2017/001729
§ 371 (c)(1),
(2) Date: May 28, 2019

(87) PCT Pub. No.: WO2018/062643
PCT Pub. Date: Apr. 5, 2018

(65) Prior Publication Data
US 2020/0030395 A1 Jan. 30, 2020

(30) Foreign Application Priority Data
Sep. 27, 2016 (KR) .................. 10-2016-0124270

(51) Int. Cl.
| | | |
|---|---|---|
| *A61K 36/07* | (2006.01) | |
| *A23L 33/105* | (2016.01) | |
| *A23L 33/125* | (2016.01) | |
| *A23L 33/135* | (2016.01) | |
| *A61P 1/10* | (2006.01) | |
| *A61P 1/12* | (2006.01) | |
| *A61K 35/745* | (2015.01) | |
| *A61K 35/747* | (2015.01) | |
| *A61K 35/00* | (2006.01) | |
| *A61K 9/00* | (2006.01) | |

(52) U.S. Cl.
CPC ............ *A61K 36/07* (2013.01); *A23L 33/105* (2016.08); *A23L 33/125* (2016.08); *A23L 33/135* (2016.08); *A61K 9/0053* (2013.01); *A61K 35/745* (2013.01); *A61K 35/747* (2013.01); *A61P 1/10* (2018.01); *A61P 1/12* (2018.01); *A23V 2002/00* (2013.01); *A23Y 2220/03* (2013.01); *A23Y 2220/67* (2013.01); *A23Y 2220/73* (2013.01); *A23Y 2300/49* (2013.01); *A23Y 2300/55* (2013.01); *A61K 2035/115* (2013.01)

(58) Field of Classification Search
CPC ........ A23L 33/105; A23L 33/125; A61P 1/10; A61P 1/12; A61K 35/745; A61K 2035/115; A61K 35/744; A23Y 2220/03; A23Y 2220/67; A23Y 2220/73; A23Y 2300/49; A23Y 2300/55; A23P 10/30; A23V 2200/3204; A23V 2250/208
See application file for complete search history.

(56) References Cited

U.S. PATENT DOCUMENTS

| 8,021,656 B2 | 9/2011 | Corthesy-Theulaz et al. |
| 9,576,403 B2 | 2/2017 | Salvador Marcos et al. |
| 9,746,595 B2 | 8/2017 | Nagaya et al. |

FOREIGN PATENT DOCUMENTS

| CN | 102919850 | * | 2/2013 |
| CN | 104887647 | * | 9/2015 |
| JP | 2010-285421 A | | 12/2010 |
| KR | 10-2003-0070799 A | | 9/2003 |
| KR | 10-2004-0062000 A | | 7/2004 |
| KR | 10-2005-0025978 A | | 3/2005 |
| KR | 10-2012-0109119 A | | 10/2012 |
| KR | 10-1274467 B1 | | 6/2013 |
| KR | 10-1401530 B1 | | 6/2014 |
| KR | 10-1446309 B1 | | 10/2014 |
| KR | 10-2015-0023370 A | | 3/2015 |
| KR | 10-2015-0023375 A | | 3/2015 |

OTHER PUBLICATIONS

Bhakta et al., International Journal of Health Sciences & Research, 77, vol. 3, Issue 8, Aug. 2013, p. 77-84.*
Magro et al., Nutrition Journal, 2014, vol. 13, No. 75, p. 1-5.*
International Search Report dated May 23, 2017, issued in corresponding International Patent Application No. PCT/KR2017/001729.
Korean Agriculture Culture Collection (KACC), International Form: Receipt in the Case of an Original Deposit for Bifidobacterium longum CBG-C11, dated Jul. 13, 2011, 5 pages.

* cited by examiner

Primary Examiner — Kade Ariani
(74) Attorney, Agent, or Firm — Hauptman Ham, LLP

(57) ABSTRACT

The present invention relates to a probiotics composition containing: lactic acid bacteria powder comprising lactic acid bacteria selected from the group consisting of *Bifidobacterium lactis*, *Bifidobacterium longum*, *Lactobacillus acidophilus*, *Lactobacillus plantarum*, and *Lactobacillus rhamnosus*; a mushroom extract; and a fructooligosaccharide.

7 Claims, No Drawings

PROBIOTICS COMPOSITION CONTAINING HERICIUM ERINACEUS

CROSS REFERENCE TO RELATED APPLICATION

This present application is a national stage filing under 35 U.S.C § 371 of PCT application number PCT/KR2017/001729 filed on Feb. 16, 2017 which is based upon and claims the benefit of priority to Korean Patent Application No. 10-2016-0124270 filed on Sep. 27, 2016 in the Korean Intellectual Property Office. The disclosures of the above-listed applications are hereby incorporated by reference herein in their entirety.

TECHNICAL FIELD

The present disclosure relates to a probiotics composition containing *hericium erinaceus*.

BACKGROUND

Recently, as influence of intestinal microorganisms on the physical and mental health of the human body has become widely known, efforts are being made to diversify kinds of intestinal microorganisms and improve the activity thereof.

The most popular and widespread one of these efforts is the ingestion of probiotics. Probiotics refers to live bacteria that have beneficial effects on the health of humans, animals, etc. Among probiotics, lactic acid bacteria such as *Lactobacillus*, *Bifidobacterium* and *Lactococcus* are widely used.

However, these probiotics have different effects on the human body depending on the kind of bacteria. There is a low probability that the probiotics as ingested live and reach desired body parts, such as the small intestine and colon. Therefore, in order to enhance the activity and lifespan of probiotics, probiotics are ingested with prebiotics.

*Hericium erinaceus* has more kinds of active polysaccharides than ordinary mushrooms. Among them, specific active polysaccharide such as galactoxyloglucan and mannoglucoxylane are contained. Thus, *hericium erinaceus* has excellent anti-tumor ability. Further, *hericium* polysaccharide, a polysaccharide known to be found only in *hericium erinaceus*, acts on bacteria or viruses or defective cells to enhance macrophages or lymphocytes, thereby preventing the development of colorectal cancer or stomach cancer. Further, *hericium* polysaccharide was found to be effective against various gastritis. Further, oleanolic acid, which is only found in some medicinal mushrooms, is contained at a large content in the *hericium erinaceus*. Thus, the *hericium erinaceus* is known to protect gastric wall and be effective against gastric ulcer and gastritis. In particular, Hericenone D and Erinacine C which promote the biosynthesis of Nerve Growth Factor (GNF), are found in *hericium erinaceus*. Thus, the *hericium erinaceus* is known to be effective in preventing and treating dementia of the elderly. Further, Hericenone D and Erinacine C contained in *hericium erinaceus* may be delivered to the brain in the blood to promote the synthesis of the Nerve Growth Factor. Thus, the *hericium erinaceus* may perform an effective treatment for Alzheimer's disease. Further, the *hericium erinaceus* inhibits the loss of neurons by promoting the synthesis of neuronal growth factors four times via the hormone epinephrine in the brain. The *hericium erinaceus* may promote the synthesis of neurons, thus to play a role in the development of intelligence of children or adolescents in the growing period. Especially, it is known that when minerals such as potassium, calcium and magnesium contained in *hericium erinaceus* enters into the body and interacts with the enzyme, ionizing metabolism signal emits to allow a low molecule material such as a peptide to be absorbed into a cell, thereby to restore the function of the beta cell and to secrete insulin. In other words, it is known that insulin is normally secreted via such a series of actions, and thus, blood sugar level is lowered, and diabetes is improved. Further, *hericium erinaceus* is well known as an agent for improving liver function.

While the present inventors were studying bioactivity-enhanced probiotics, we have evaluated the enhancement of intestinal health by ingesting specific probiotics with *hericium erinaceus* extract. In this way, the present disclosure has been achieved.

DISCLOSURE

Technical Purpose

A purpose of the present disclosure is to provide a probiotics composition with enhanced bioactivity.

Technical Solution

In order to achieve the purpose, the present disclosure provides a probiotics composition containing: lactic acid bacteria powders containing lactic acid bacteria selected from a group consisting of *Bifidobacterium lactis, Bifidobacterium longum, Lactobacillus acidophilus, Lactobacillus plantarum,* and *Lactobacillus rhamnosus*; a mushroom extract; and a fructooligosaccharide.

Technical Effect

The probiotics composition according to the present disclosure improves intestine health, ameliorates constipation and ameliorates diarrhea and intestine pain.

BEST MODE

The present disclosure provides a probiotics composition containing: lactic acid bacteria powders containing lactic acid bacteria selected from a group consisting of *Bifidobacterium lactis, Bifidobacterium longum, Lactobacillus acidophilus, Lactobacillus plantarum,* and *Lactobacillus rhamnosus*; a mushroom extract; and a fructooligosaccharide.

Further, the present disclosure provides a method for ameliorating constipation, the method including orally-administering a probiotics composition to a subject, wherein the probiotics composition contains: lactic acid bacteria powders containing lactic acid bacteria selected from a group consisting of *Bifidobacterium lactis, Bifidobacterium longum, Lactobacillus acidophilus, Lactobacillus plantarum,* and *Lactobacillus rhamnosus*; a mushroom extract; and a fructooligosaccharide.

Furthermore, the present disclosure provides a method for ameliorating diarrhea and intestine pain, the method including orally-administering a probiotics composition to a subject, wherein the probiotics composition contains: lactic acid bacteria powders containing lactic acid bacteria selected from a group consisting of *Bifidobacterium lactis, Bifidobacterium longum, Lactobacillus acidophilus, Lactobacillus plantarum,* and *Lactobacillus rhamnosus*; a mushroom extract; and a fructooligosaccharide.

Furthermore, the present disclosure is directed to use of a probiotics composition for ameliorating constipation, wherein the probiotics composition contains: lactic acid bacteria powders containing lactic acid bacteria selected from a group consisting of *Bifidobacterium lactis, Bifidobacterium longum, Lactobacillus acidophilus, Lactobacillus plantarum*, and *Lactobacillus rhamnosus*; a mushroom extract; and a fructooligosaccharide.

Furthermore, the present disclosure is directed to use of a probiotics composition for ameliorating diarrhea and intestine pain, wherein the probiotics composition contains: lactic acid bacteria powders containing lactic acid bacteria selected from a group consisting of *Bifidobacterium lactis, Bifidobacterium longum, Lactobacillus acidophilus, Lactobacillus plantarum*, and *Lactobacillus rhamnosus*; a mushroom extract; and a fructooligosaccharide.

The following describes the present disclosure in detail.

Lactic Acid Bacteria Powders

The lactic acid bacteria powder in accordance with the present disclosure contains lactic acid bacteria selected from a group consisting of *Lactococuus, lactis, Enterococcus faecium, Enterococcus faecalis, Streptococcus thermophilus, Bifidobacterium lactis, Bifidobacterium longum, Bifidobacterium bifidum, Bifidobacterium breve, Bifidobacterium animalis* ssp. *lactis, Lactobacillus acidophilus, Lactobacillus casei, Lactobacillus gasseri, Lactobacillus delbrueckii* ssp. *bulgaricus, Lactobacillus helveticus, Lactobacillus fermentum, Lactobacillus paracasei, Lactobacillus reuteri, Lactobacillus salivarius, Lactobacillus plantarum*, and *Lactobacillus rhamnosus*. Preferably, the lactic acid bacteria powder in accordance with the present disclosure contains *Lactococuus lactis, Enterococcus faecium, Enterococcus faecalis, Streptococcus thermophilus, Bifidobacterium lactis, Bifidobacterium longum, Bifidobacterium bifidum, Bifidobacterium breve, Bifidobacterium animalis* ssp. *lactis, Lactobacillus acidophilus, Lactobacillus casei, Lactobacillus gasseri, Lactobacillus delbrueckii* ssp. *bulgaricus, Lactobacillus helveticus, Lactobacillus fermentum, Lactobacillus paracasei, Lactobacillus reuteri, Lactobacillus salivarius, Lactobacillus plantarum* and *Lactobacillus rhamnosus*. More preferably, the lactic acid bacteria powder in accordance with the present disclosure includes *Lactococuus lactis, Enterococcus faecium, Enterococcus faecalis, Streptococcus thermophilus, Bifidobacterium lactis, Bifidobacterium longum, Bifidobacterium bifidum, Bifidobacterium breve, Bifidobacterium animalis* ssp. *lactis, Lactobacillus acidophilus, Lactobacillus casei, Lactobacillus gasseri, Lactobacillus delbrueckii* ssp. *bulgaricus, Lactobacillus helveticus, Lactobacillus fermentum, Lactobacillus paracasei, Lactobacillus reuteri, Lactobacillus salivarius, Lactobacillus plantarum, Lactobacillus rhamnosus*, and a *Bifidobacterium lactis*-containing double-micro capsule powder.

In this connection, except for the *Bifidobacterium lactis*-containing double-micro capsule powder, all of the remaining lactic acid bacteria do not have a form of a double-micro capsule. The lactic acid bacteria that do not have the double-micro capsule may or may not be coated in a form of other capsules.

The lactic acid bacteria powders according to the present disclosure contain the *Bifidobacterium lactis* having a form of the double-micro capsule powder and *Bifidobacterium lactis* not having the form of the double-micro capsule at a weight ratio of 1:0.5 to 1.5, preferably, at a weight ratio of 1:0.8 to 1.2, more preferably, at a weight ratio of 1:1.

The *Bifidobacterium lactis* is preferably *Bifidobacterium lactis* CBG-C10 (Deposition Number KACC 15464). The *Bifidobacterium longum* is preferably *Bifidobacterium longum* CBG-C11 (Deposition Number KCTC 11979BP). The *Lactobacillus acidophilus* is preferably *Lactobacillus acidophilus* CBG-C13 (Deposition Number KACC 91980P). The *Lactobacillus acidophilus* CBG-C13 was deposited to Korean Agricultural Culture Collection (KACC) (New address due to location change: 166, Nongsaengmyeong-ro, Iseo-myeon, Wanju-gun, Jeollabuk-do 55365, Republic of Korea) in the Center of Agricultural Genetic Resources of National Institute of Agricultural Sciences on Sep. 30, 2014, and a Deposition Number was assigned as KACC 91980P. The *Lactobacillus plantarum* is preferably *Lactobacillus plantarum* JBMI F5 (Deposition Number KACC 91638P). The *Lactobacillus rhamnosus* is preferably *Lactobacillus rhamnosus* CBG-C14 (Deposition Number KACC 91981P). The *Lactobacillus rhamnosus* CBG-C14 was deposited to Korean Agricultural Culture Collection (KACC) (New address due to location change: 166, Nongsaengmyeong-ro, Iseo-myeon, Wanju-gun, Jeollabuk-do 55365, Republic of Korea) in the Center of Agricultural Genetic Resources of National Institute of Agricultural Sciences on Sep. 30, 2014, and a Deposition Number was assigned as KACC 91981P.

In particular, the probiotics composition according to the present disclosure preferably contains *Lactobacillus acidophilus* CBG-C13 (Deposition Number KACC 91980P) and *Lactobacillus rhamnosus* CBG-C14 (Deposition Number KACC 91981P).

Further, contents of Korean patent No. 10-1446309, 10-1401530 and 10-1274467, and Korean Patent Application No. 10-2015-0023370 and 10-2015-0023375 are incorporated herein by reference in their entirety.

Mushroom Extract

The mushroom extract according to the present disclosure is preferably *hericium erinaceus* extract. Further preferably, the mushroom extract according to the present disclosure is an extract of *hericium erinaceus* fruit body, an extract of *hericium erinaceus* mycelium, or an extract of *hericium erinaceus* fruit body and mycelium. Preferably, the extract is a water extract or a low-alcohol extract having a carbon number of 5 or smaller. More preferably, the extract is a water extract or a low-alcohol extract having a carbon number of 3 or smaller. Most preferable, the extract is an ethanol extract. In this connection, the ethanol extract is preferably extracted with a solvent containing ethanol and water. Adding the *hericium erinaceus* extract into the probiotics composition according to the present disclosure may allow the in vivo activity of the lactic acid bacteria to be enhanced. It is preferable to use dextrin together with the *hericium erinaceus* extract in the production of the probiotics composition according to the present disclosure. In this connection, mixing of the dextrin and the *hericium erinaceus* extract at a weight ratio of 10:15 to 30 is advantageous for preventing the accumulation of the probiotics composition due to the high viscosity of the *hericium erinaceus* extract and thus achieving uniform and dry powders.

Probiotics Composition

The probiotics composition according to the present disclosure may diversify the types of intestinal microorganisms and enhance the in vivo activity of beneficial microorganisms in the intestines. The probiotics composition according to the present disclosure may inhibit the activity of the harmful bacteria in the intestines to promote intestinal health. The probiotics composition according to the present disclosure may ameliorate constipation in a subject with constipation and may have the effect of ameliorating diarrhea and intestine pain in a subject with diarrhea and intestine pain. That is, the probiotics composition according to the present disclosure improves intestinal health and helps defecation.

Subject

The subject orally taking the probiotics composition according to the present disclosure is a mammal including human. The subject includes, but is not limited to, people with constipation, people with diarrhea and intestine pain, and people with intestine problems.

The probiotics composition according to the present disclosure is preferably provided in a form of powders. For example, The probiotics composition according to the present disclosure may be provided in the form of preparations for oral administration, for example, in the form of tablets, hard or soft capsules, liquids, suspensions, and the like. These preparations may be prepared using acceptable conventional carriers, for example, excipients, binders, disintegrants, lubricants, solubilizers, suspending agents, preservatives or extenders for preparations for oral administration.

MODE

The advantages and features of the present disclosure, and the method for achieving the same will become clearer with reference to the Present Examples, which are described in detail below. However, the present disclosure is not limited to the Present Examples as described below, but may be implemented in various different forms. Only the Present Examples make the present disclosure complete. The Present Examples are provided to fully inform the category of the present disclosure to those of ordinary skill in the art to which it belongs. The scope of the present disclosure is only defined by the claims.

<Material and Method>

As the lactic acid bacteria, lactic acid bacteria shown in Table 1 were used. The lactic acid bacteria were provided from Chebigen Corporation in South Korea. *Bifidobacterium lactis* CBG-C10-containing double-micro capsule powders were also provided from Chebigen Corporation in South Korea. *Lactobacillus acidophilus* CBG-C13 (Deposition Number KACC 91980P) and *Lactobacillus rhamnosus* CBG-C14 (Deposition Number KACC 91981P) have acid resistance, bile-acid resistance, and antibiotic resistance. Especially, *Lactobacillus acidophilus* CBG-C13 (Deposition Number KACC 91980P) and *Lactobacillus rhamnosus* CBG-C14 (Deposition Number KACC 91981P) have excellent effect on the proliferation of intestinal beneficial bacteria and inhibition of harmful bacteria, thereby to improve defecation.

The fruit body and mycelium of the *hericium erinaceus* were originated from the domestic purchased *hericium erinaceus*. *Flammulina velutipes* and *Lentinus edodes* were purchased from the commercial mushroom market.

<Production Example 1> Production of *Hericium Erinaceus* Fruit Body Powders

After 10 kg of *hericium erinaceus* fruit body was cleaned, and then, the *hericium erinaceus* fruit body was dried at a temperature of 40 to 60° C. for 20 hours or longer in a cylindrical stainless steel decompression dryer, thereby obtain the dried *hericium erinaceus* fruit body having a water content of 3% or lower. The dried *hericium erinaceus* fruit body was milled with a pin mill to produce *hericium erinaceus* fruit body powders having about 50 mesh size.

<Production Example 2> Production of *Hericium Erinaceus* Mycelium Powders

After 10 kg of *hericium erinaceus* mycelium was cleaned, and then, the *hericium erinaceus* mycelium was dried at a temperature of 40 to 60° C. for 20 hours or longer in a cylindrical stainless steel decompression dryer, thereby obtain the dried *hericium erinaceus* mycelium having a water content of 3% or lower. The dried *hericium erinaceus* mycelium was milled with a pin mill to produce *hericium erinaceus* mycelium powders having about 50 mesh size.

<Production Example 3> Production of *Hericium Erinaceus* Extract A 5 kg of the *hericium erinaceus* fruit body powders produced in Production Example 1 were added to a mixed solvent of 2.5 L of ethanol and 10 L of water to form a mixed solution. Then, the mixed solution was input into a 100 L of stainless steel container with a reflux device and then was heated at 90 to 98° C. for 24 hours, thereby to obtain a crude extract of the *hericium erinaceus* fruit body. Then, after filtering the crude extract with a nonwoven filter, the mixed solvent was distilled in a decompression distilling manner to produce 500 mL of concentrated liquid *hericium erinaceus* fruit body extract, which, in turn, was dried in hot air and then pulverized to produce the *hericium erinaceus* extract A.

TABLE 1

| Species | Strain name | Korean patent (patent application) No. | Deposition Number |
|---|---|---|---|
| *Bifidobacterium lactis* | *Bifidobacterium lactis* CBG-C10 | Korean Patent No: 10-1446309 | KACC 15464 |
| *Bifidobacterium longum* | *Bifidobacterium longum* CBG-C11 | Korean Patent No: 10-1401530 | KCTC 11979BP |
| *Lactobacillus acidophilus* | *Lactobacillus acidophilus* CBG-C13 | Korean patent application No: 10-2015-0023370 | KACC 91980P |
| *Lactobacillus plantarum* | *Lactobacillus plantarum* JBMI F5 | Korean Patent No: 10-1274467 | KACC 91638P |
| *Lactobacillus rhamnosus* | *Lactobacillus rhamnosus* CBG-C14 | Korean patent application No: 10-2015-0023375 | KACC 91981P |

<Production Example 4> Production of *Hericium Erinaceus* Extract B 5 kg of the *hericium erinaceus* mycelium powders produced in Production Example 2 were added to a mixed solvent of 2.5 L of ethanol and 10 L of water to form a mixed solution. Then, the mixed solution was input into a 100 L of stainless steel container with a reflux device and then was heated at 90 to 98° C. for 24 hours, thereby to obtain a crude extract of the *hericium erinaceus* mycelium. Then, after filtering the crude extract with a nonwoven filter, the mixed solvent was distilled in a decompression distilling manner to produce 500 mL of concentrated liquid *hericium erinaceus* mycelium extract, which, in turn, was dried in hot air and then pulverized to produce the *hericium erinaceus* extract B.

<Production Example 5> Production of *Hericium Erinaceus* Extract C 3.5 kg of *hericium erinaceus* fruit body powders produced in Production Example 1 and 1.5 kg of *hericium erinaceus* mycelium powders produced in Production Example 2 were mixed to produce a mixture of *hericium erinaceus* powders. Then, 5 kg of the mixture of *hericium erinaceus* powders was added to a mixed solvent of 2.5 L of ethanol and 10 L of water to form a mixed solution. Then, the mixed solution was input into a 100 L of stainless steel container with a reflux device and then was heated at 90 to 98° C. for 24 hours, thereby to obtain a crude extract of the *hericium erinaceus* mycelium and fruit body. Then, after filtering the crude extract with a nonwoven filter, the mixed solvent was distilled in a decompression distilling manner to produce 500 mL of concentrated liquid *hericium erinaceus* mycelium and fruit body extract, which, in turn, was dried in hot air and then pulverized to produce the *hericium erinaceus* extract C.

<Production Example 6> Production of *Lentinus Edodes* Extract Powders

After 10 kg of *Lentinus edodes* was cleaned, and then, the *Lentinus edodes* was dried at a temperature of 40 to 60° C. for 20 hours or longer in a cylindrical stainless steel decompression dryer, thereby obtain the dried *Lentinus edodes* having a water content of 3% or lower. The dried *Lentinus edodes* was milled with a pin mill to produce *Lentinus edodes* powders. 5 kg of the *Lentinus edodes* powders produced above were added to a mixed solvent of 2.5 L of ethanol and 10 L of water to form a mixed solution. Then, the mixed solution was input into a 100 L of stainless steel container with a reflux device and then was heated at 90 to 98° C. for 24 hours, thereby to obtain a crude extract of the *Lentinus edodes*. Then, after filtering the crude extract with a nonwoven filter, the mixed solvent was distilled in a decompression distilling manner to produce 500 mL of concentrated liquid *Lentinus edodes* extract, which, in turn, was dried in hot air and then pulverized to produce the *Lentinus edodes* extract powders.

<Production Example 7> Production of *Flammulina Velutipes* Extract Powders

After 10 kg of *Flammulina velutipes* was cleaned, and then, the *Flammulina velutipes* was dried at a temperature of 40 to 60° C. for 20 hours or longer in a cylindrical stainless steel decompression dryer, thereby obtain the dried *Flammulina velutipes* having a water content of 3% or lower. The dried *Flammulina velutipes* was milled with a pin mill to produce *Flammulina velutipes* powders. 5 kg of the *Flammulina velutipes* powders produced above were added to a mixed solvent of 2.5 L of ethanol and 10 L of water to form a mixed solution. Then, the mixed solution was input into a 100 L of stainless steel container with a reflux device and then was heated at 90 to 98° C. for 24 hours, thereby to obtain a crude extract of the *Flammulina velutipes*. Then, after filtering the crude extract with a nonwoven filter, the mixed solvent was distilled in a decompression distilling manner to produce 500 mL of concentrated liquid *Flammulina velutipes* extract, which, in turn, was dried in hot air and then pulverized to produce the *Flammulina velutipes* extract powders.

Present Example 1

Production of Lactic Acid Bacteria Powders 10 parts by weight of milk was added to 100 parts by weight of distilled water to form a mixture which was sterilized. Then, 2 parts by weight of lactic acid bacteria was inoculated into the mixture, and was cultured at 38 degrees C. for 10 hours and was subjected to lyophilization. Thus, lactic acid bacteria powders were prepared.

In this connection, the lactic acid bacteria employed a mixture of *Bifidobacterium lactis, Bifidobacterium longum, Lactobacillus acidophilus, Lactobacillus plantarum, Lactobacillus rhamnosus*, and a *Bifidobacterium lactis*-containing double-micro capsule powder at the same weight content.

Production of Probiotics Composition

A probiotics composition was prepared by adding, to 100 parts by weight of the lactic acid bacteria powders, 250 parts by weight of the *hericium erinaceus* extract A as produced in the Production Example 3, 10 parts by weight of vitamin C, 50 parts by weight of fructooligosaccharide, 20 parts by weight of glucose anhydrocrystalline, 10 parts by weight of tagatose, 10 parts by weight of enzymatically modified *stevia*, 10 parts by weight of berry flavor powders, 100 parts by weight of dextrin, and 10 parts by weight of silicon dioxide.

Present Example 2

A probiotics composition was produced in the same manner as in Present Example 1 except that the *hericium erinaceus* extract B was used instead of the *hericium erinaceus* extract A.

Present Example 3

A probiotics composition was produced in the same manner as in Present Example 1 except that the *hericium erinaceus* extract C was used instead of the *hericium erinaceus* extract A.

Present Example 4

A probiotics composition was produced in the same manner as in Present Example 1 except that the *Lentinus edodes* extract powders were used instead of the *hericium erinaceus* extract A.

Present Example 5

A probiotics composition was produced in the same manner as in Present Example 1 except that the *Flammulina velutipes* extract powders were used instead of the *hericium erinaceus* extract A.

Present Example 6

The probiotics composition was produced in the same manner as in Present Example 1 except that the *hericium erinaceus* extract A was not used. That is, in Present Example 6, the mushroom extract was not used at all as the prebiotics.

Present Example 7

The probiotics composition was produced in the same manner as in Present Example 1 except that the *Bifidobacterium lactis*-containing double-micro capsule powders were not used in the lactic acid bacteria powders production.

Present Example 8

The probiotics composition was produced in the same manner as in Present Example 1 except that *Lactobacillus acidophilus* CBG-C13 (Deposition Number KACC 91980P) was not used in the lactic acid bacteria powders production.

Present Example 9

The probiotics composition was produced in the same manner as in Present Example 1 except that *Lactobacillus rhamnosus* CBG-C14 (Deposition Number KACC 91981P) was not used in the lactic acid bacteria powders production.

Experimental Example 1

The subjects were 90 males and females aged 16 to 42 with constipation. We assessed whether the probiotics composition according to the present disclosure contributed to defecation ability of the subjects. In this connection, each of the probiotics compositions of Present Examples 1 to 9 was taken twice a day by each group of 10 patients. Then, a frequency of defecation was recorded. A single dose was 60 g.

After 2 months, whether times of the defecations increase compared to those prior to the experiment was evaluated. As a result, the probiotics compositions of Present Examples 1 to 4 were evaluated to be excellent in ameliorating the constipation in people with constipation symptom. Further, the probiotics compositions of Present Examples 7 and 8 ameliorated the constipation and have varying ameliorating effects between the subjects (Table 2).

TABLE 2

|  | Constipation being greatly ameliorated | Constipation being somewhat ameliorated | No meaningful difference | Constipation being somewhat worsened | Constipation being greatly worsened |
|---|---|---|---|---|---|
| Present Example 1 | 4 | 3 | 3 |  |  |
| Present Example 2 | 2 | 6 | 2 |  |  |
| Present Example 3 | 3 | 4 | 3 |  |  |
| Present Example 4 |  | 1 | 7 | 1 | 1 |
| Present Example 5 |  | 3 | 5 | 1 | 1 |
| Present Example 6 | 1 | 5 | 3 | 1 |  |
| Present Example 7 | 1 | 4 | 5 |  |  |
| Present Example 8 |  | 6 | 3 |  |  |
| Present Example 9 |  | 5 | 2 | 3 |  |

Experimental Example 2

Subjects were 36 men and women aged 18 to 43 who had frequent intestine pain or frequently had diarrhea due to intestine trouble. The improving ability of intestine health by the probiotics composition according to the present disclosure was evaluated for the subjects. In this connection, each of the probiotics compositions of Present Examples 1 to 9 was taken twice a day by each group of 10 patients. Then, a frequency of defecation was recorded. A single dose was 60 g.

After two months, whether times of diarrheas and intestine pains decrease compared to those prior to the experiment was evaluated. As a result, the probiotics compositions of Present Examples 1 to 3 showed excellent improving ability of intestine health. The probiotics composition of the Present Example 7 showed the improving ability of intestine health for some subjects but did not show the improving ability of intestine health for the other subjects (Table 3).

C, 50 parts by weight of fructooligosaccharide, 20 parts by weight of glucose anhydrocrystalline, 10 parts by weight of tagatose, 10 parts by weight of enzymatically modified *stevia*, 10 parts by weight of berry flavor powders, and 10 parts by weight of silicon dioxide.

TABLE 3

|  | Intestine trouble being considerably ameliorated | Intestine trouble being somewhat ameliorated | No meaningful difference | Intestine trouble being somewhat being worsened | Intestine trouble being considerably worsened |
|---|---|---|---|---|---|
| Present Example 1 | 3 | 6 | 1 |  |  |
| Present Example 2 | 2 | 5 | 3 |  |  |
| Present Example 3 | 4 | 4 | 2 |  |  |
| Present Example 4 |  | 2 | 6 | 1 | 1 |
| Present Example 5 |  | 1 | 5 | 2 | 1 |
| Present Example 6 | 1 | 2 | 6 |  | 1 |
| Present Example 7 | 1 | 3 | 6 |  |  |
| Present Example 8 | 1 | 2 | 3 | 4 |  |
| Present Example 9 |  | 3 | 4 | 1 | 2 |

Experimental Example 3

Production of Lactic Acid Bacteria Powders 10 parts by weight of milk was added to 100 parts by weight of distilled water to form a mixture which was sterilized. Then, 2 parts by weight of lactic acid bacteria was inoculated into the mixture, and was cultured at 38 degrees C. for 10 hours and was subjected to lyophilization. Thus, lactic acid bacteria powders were prepared.

In this connection, the lactic acid bacteria employed a mixture between the lactic acid bacteria mixture of the <Table 1> and commercially available lactic acid bacteria mixture at a weight ratio of 1:1.

That is, the lactic acid bacteria mixture of the <Table 1> was a mixture of *Bifidobacterium lactis, Bifidobacterium longum, Lactobacillus acidophilus, Lactobacillus plantarum, Lactobacillus rhamnosus* and a *Bifidobacterium lactis*-containing double-micro capsule powder at the same weight content.

The commercially available lactic acid bacteria mixture was a mixture of commercially available *Lactococuus lactis, Enterococcus faecium, Enterococcus faecalis, Streptococcus thermophilus, Bifidobacterium bifidum Bifidobacterium breve, Bifidobacterium animalis* ssp. *lactis, Lactobacillus casei, Lactobacillus gasseri, Lactobacillus delbrueckii* ssp. *bulgaricus, Lactobacillus helveticus, Lactobacillus fermentum, Lactobacillus paracasei, Lactobacillus reuteri* and *Lactobacillus salivarius* powders at the same weight content.

Then, the lactic acid bacteria employed a mixture between the lactic acid bacteria mixture of the <Table 1> and the commercially available lactic acid bacteria mixture were mixed at a weight ratio of 1:2 to produce the lactic acid bacteria mixture powders.

Production of Probiotics Composition

A probiotics composition was prepared by adding, to 100 parts by weight of the lactic acid bacteria powders, 250 parts by weight of the *hericium erinaceus* extract A as produced in the Production Example 3, 10 parts by weight of vitamin The probiotics composition was orally administered into, as the subjects, 20 men and women aged 60 to 84 years with constipation, to evaluate the defecation helplessness of the probiotics composition. In this connection, the probiotics composition was taken twice a day by the subjects. Then, a frequency of defecation was recorded. A single dose was 60 g.

As a result, the constipation was significantly ameliorated for 4 out of 20 subjects and the constipation was somewhat ameliorated for 11 out of the 20 subjects.

INDUSTRIAL AVAILABILITY

The present disclosure provides a probiotics composition containing: lactic acid bacteria powders containing lactic acid bacteria selected from a group consisting of *Bifidobacterium lactis, Bifidobacterium longum, Lactobacillus acidophilus, Lactobacillus plantarum*, and *Lactobacillus rhamnosus*; a mushroom extract; and a fructooligosaccharide.

What is claimed is:

1. A method for ameliorating constipation, the method including orally-administering a probiotics composition to a subject, wherein the probiotics composition contains:
   lactic acid bacteria powders containing lactic acid bacteria comprises:
      at least one selected from the group consisting of *Bifidobacterium lactis, Bifidobacterium longum, Lactobacillus acidophilus, Lactobacillus plantarum*, and *Lactobacillus rhamnosus*; and
      at least one selected from the group consisting of *Lactococuus lactis, Enterococcus faecium, Enterococcus faecalis, Streptococcus thermophilus, Bifidobacterium bifidum, Bifidobacterium breve, Bifidobacterium animalis* ssp. *lactis, Lactobacillus casei, Lactobacillus gasseri, Lactobacillus delbrueckii* ssp. *bulgaricus, Lactobacillus helveticus, Lactobacillus fermentum, Lactobacillus paracasei, Lactobacillus reuteri*, and *Lactobacillus salivarius;*
   a mushroom extract; and
   a fructooligosaccharide.

2. The method for ameliorating constipation of claim 1, wherein the probiotics composition further comprises *Bifidobacterium lactis*-containing double-micro capsule powders.

3. The method for ameliorating constipation of claim 1, wherein the lactic acid bacteria comprises the *Lactobacillus acidophilus*, and the *Lactobacillus acidophilus* is *Lactobacillus acidophilus* CBG-C13 (Deposition Number KACC 91980P).

4. The method for ameliorating constipation of claim 1, wherein the lactic acid bacteria comprises the *Lactobacillus rhamnosus*, and the *Lactobacillus rhamnosus* is *Lactobacillus rhamnosus* CBG-C14 (Deposition Number KACC 91981P).

5. The method for ameliorating constipation of claim 1, wherein the lactic acid bacteria comprises *Bifidobacterium lactis*, and wherein a weight ratio between *Bifidobacterium lactis* present in a form of a double-micro capsule and *Bifidobacterium lactis* not present in the form of the double-micro capsule ranges from 1:0.5 to 1:1.5.

6. The method for ameliorating constipation of claim 1, wherein the mushroom extract comprises a *Hericium erinaceus* extract.

7. The method for ameliorating constipation of claim 1, wherein the mushroom extract comprises a *Hericium erinaceus* fruit body extract.

* * * * *